(12) United States Patent
Davar (10) Patent No.: US 6,673,832 B1
(45) Date of Patent: Jan. 6, 2004

(54) METHODS FOR IDENTIFYING COMPOUNDS FOR TREATING PAIN

(76) Inventor: Gudarz Davar, Eight Myrtle St., Jamaica Plain, MA (US) 02130

( * ) Notice: Subject to any disclaimer, the term of this patent is extended or adjusted under 35 U.S.C. 154(b) by 0 days.

(21) Appl. No.: 09/072,428

(22) Filed: May 4, 1998

(51) Int. Cl.$^7$ .............................................. C07C 229/36
(52) U.S. Cl. ....................... 514/466; 514/562; 514/563; 514/538; 514/539; 424/534; 424/569; 424/578
(58) Field of Search ................................. 514/562, 563, 514/538, 539, 567, 63, 466, 617, 464; 424/534, 569, 578

(56) References Cited

U.S. PATENT DOCUMENTS

| | | | |
|---|---|---|---|
| 5,504,215 A | | 4/1996 | Talley et al. ............. 548/377.1 |
| 5,648,486 A | * | 7/1997 | Cai et al. .................... 544/124 |
| 5,658,943 A | * | 8/1997 | Berryman et al. .......... 514/466 |
| 5,800,385 A | * | 9/1998 | Demopulos et al. .......... 604/49 |

OTHER PUBLICATIONS

Avellino et al., "Differential Macrophage Responses in the Peripheral and Central Nervous System during Wallerian Degeneration of Axons." *Exp. Neurol.*, 136:183–194 (1995).
Cheng et al., "Endothelin Inhibitors." *Annual Reports in Medicinal Chemistry*, 32:61–70 (1997).
Clatworthy et al., "Role of Peri–Axonal Inflammation in the Development of Thermal Hyperalgesia and Guarding Behavior in a Rat Model of Neuropathic Pain." *Neurosci. Lett.*, 184:5–9 (1995).
Dahlin, "Prevention of Macrophage Invasion Impairs Regeneration in Nerve Grafts." *Brain Res.* 679:274–280 (1992).
Dahlof et al., "Regional Hemodynamic Effects of Endothelin–1 in Rat and Man: Unexpected Adverse Effects." *J. Hypertension*, 8:811–817 (1990).
Danielson et al., "Inflammatory Cells and Mediators in the Silicone Chamber Model for Nerve Regeneration." *Biomaterials*, 14:1180–1185 (1993).
Dashwood et al., "Neurovascular [125I]–ET–1 Binding Sites on Human Peripheral Nerve." *Endothelium*, 5:119–123 (1997).
Davar et al., "MK–801 Blocks the Development of Thermal Hyperalgesia in a Rat Model of Experimental Painful Neuropathy." *Brain Res.*, 553:327–330 (1991).
Ferreira et al., "Endothelin–1 Participation in Overt and Inflammatory Pain." *Journal of Cardiovascular Pharmacology*, 13:S220–S222 (1989).
Hickey et al., "Characterization of a Coronary Vasoconstrictor Produced by Cultured Endothelial Cells." *Am. J. Physiol*, 248:C550–C556 (1985).
Johansson and Bennett, "Effect of Local Methylprednisolone on Pain in a Nerve Injury Model." *Reg. Anesth*, 22:59–65 (1997).
Marsault et la., "Receptor Externalization Determines Sustained Contractile Responses to Endothelin–1 in the Rat Aorta." *Am. J. Physiol*, 264:C687–C693 (1993).
Monaco et al., "MHC–Positive, Ramified Macrophages in the Normal and Injured Rat Peripheral Nervous System." *J. Neurocytol.*, 21:623–634 (1992).
Nelson et al., "Identification of Endothelin–1 in a Pathophysiology of Metastatic Adenocarcinoma of the Prostate." *Nature Medicine*, 1:944–949 (1995).
Perry et al., "The Macrophage Response to Central and Peripheral Nerve Injury: A Possible Role for Macrophages in Regneration." *J. Exp. Med.*, 165:1218–1223 (1987).
Piovezan et al., "Endothelins Potentiate Formalin–Induced Nociception and Paw Edema in Mice." *Can. J. Physiol. Opharmacol.*, 75:596–600 (1997).
Raffa et al., "Characterization of Endothelin–Induced Nociception in Mice: Evidence for a Mechanistically Distinct Analgesic Model." *Pharmacol. Exp. Ther.*, 278:1–7 (1996).
Raffa et al., "Endothelin–Induced Nociception in Mice: Mediation by $ET_A$ and $ET_B$ Receptors." *J. Pharmacol. Exp. Ther.*, 276:647–651 (1996).
Sommer et al., "Pathology of Experimental Compression Neuropathy Producing Hyperesthesia." *J. Neuropathol. Exp. Neurol.*, 52:223–233 (1993).
Watkins et al., "Characterization of Cytokine–Induced Hyperalgesia." *Brain Res.*, 654:15–26 (1994).
Yanagisawa et al., "A Novel Potent Vasoconstrictor Peptide Produced by Vascular Endothelial Cells." *Nature*, 332:411–415 (1988).
Zochodne et al., "Acute Endoneurial Ischemia Induced by Epineurial Endothelin in the Rat Sciatic Nerve." *Am. J. Physiol.*, 263:H1806–H1810 (1992).

* cited by examiner

Primary Examiner—Christopher R. Tate
Assistant Examiner—Roy Teller
(74) Attorney, Agent, or Firm—Clark & Elbing LLP (57) ABSTRACT

The invention provides a method of determining whether a compound alleviates vasoconstriction-independent nerve pain mediated by endothelin-1 (ET-1). The method involves (i) determining whether the compound has the ability to inhibit a vasoconstriction-independent ET-1 action, and, if the compound has the inhibitory ability, then ii) determining whether the compound reduces vasoconstriction-independent nerve pain by testing the compound in human patients suffering from pain mediated by the vasoconstriction-independent ET-1 action. The invention also includes a method of determining whether a compound alleviates pain caused by nerve injury in human patients. The method involves (i) determining whether the compound has the ability to inhibit an inflammatory leukocyte response, and, if the compound has the inhibitory ability, then (ii) testing the compound in human patients suffering from pain caused by nerve injury to determine whether the compound alleviates the pain.

4 Claims, 11 Drawing Sheets

▼ Operated hindpaw
▽ Unoperated hindpaw

FIG. 8B

▼ Operated hindpaw
▽ Unoperated hindpaw

▼ Operated hindpaw
▽ Unoperated hindpaw

FIG. 10B

▼ Operated hindpaw
▽ Unoperated hindpaw

METHODS FOR IDENTIFYING COMPOUNDS FOR TREATING PAIN

BACKGROUND OF THE INVENTION

This invention relates to the treatment of pain and the identification of targets for pain treatment.

The sensation of pain can be caused by damage to sensory nerves (neuropathy), as well as damage to non-neural tissues. Pain that results from neuropathy is often referred to the deafferented regions of the body surface (Davar and Maciewicz, Neurol. Clin. 7: 289–304, 1989). In humans, painful peripheral neuropathy is often persistent, disabling and resistant to treatment with analgesic drugs including morphine (Sweet, Neurosurg. 15: 928–932, 1984).

Painful neuropathy often results from the direct effects of diseases, such as diabetes, varicella zoster virus (shingles) infection, trauma, autoimmune disorders, and connective tissue diseases. Alternatively, pain can result as a consequence of disease treatment, as is often observed in patients with AIDS and cancer who receive chemotherapy, radiation therapy or surgery.

One candidate mediator of pain associated with nerve injury is the inflammation response (Hafer-Macko et al., Ann. Neurol. 39: 625–635, 1995; Swartz et al., J. Neuropathol. 15:9–10, 1995; Schmidt et al., Muscle and Nerve 19: 474–487, 1996). The inflammation response in the nerve includes local edema, disruption of the perineurium, Wallerian degeneration, and infiltration of the endoneurium by progressively increasing numbers of leukocytes (Sommer et al., J. Neuropathol. Exp. Neurol. 52: 223–233, 1993; Sommer et al., J. Neuropathol. Exp. Neurol 54: 635–643, 1995). Such signs of inflammation are well developed following trauma to the rat sciatic nerve (Avellino et al., Exp. Neurol. 136: 183–194, 1995; Dahlin, Neurosci. Lett. 184: 5–8, 1992; Danielsen et al., Biomaterials 14: 1180–1185, 1993; Monaco et al., J. Neurocytol. 21: 623–634, 1992; Perry et al., J. Exp. Med. 165: 1218–1223, 1987).

Another potential mediator of nerve pain is the potent vasoconstrictor peptide, endothelin-1 (ET-1) (Hickey et al., Am. J. Physiol. 248: C550–C556, 1985; Yanagisawa et al., Nature 332: 411–415, 1988). Administration of epinephrine ($\geq 10$ nM) is known to reduce sciatic endoneurial blood flow to a degree similar to that observed with similar concentrations of ET-1 (Zochodne et al., Am. J. Physiol. 263 (Heart Circ. Physiol. 32): H1806–H1810, 1992). The intraperitoneal administration of ET-1 produces an abdominal writhing response in rodents that is ET-1 receptor-mediated. This response may be behavioral evidence of acute pain (Raffa et al., Exp. Ther. 276: 647–651, 1996a; Raffa et al., J. Pharmacol. Exp. Ther. 278: 1–7, 1996b). In humans, the intra-arterial administration of ET-1 is reported to induce severe pain that is associated with prolonged touch-evoked allodynia in the injected limb (Dahlof et al., J. Hypertension 8: 811–818, 1990). The $ET_A$ subtype receptor-dependent effects are G-protein coupled and may be linked to L-type calcium channel signaling as observed in other tissues (Reynolds et al., Biochem. Biophys. Res. Commun. 160: 868–873, 1989). ET-1 is secreted in high concentrations by metastatic prostate cancer cells (Nelson et al., Nature Medicine 1(9): 944–949, 1995).

Cancer pain affects over 75% of patients with metastatic cancer. Thus, over 1 million patients in the United States and well over 9 million patients worldwide suffer cancer pain (Bonica, The Management of Pain, second edition, ed: J. J. Bonica, pages 400–460, 1990). The pain is often debilitating and difficult to treat, especially in patients with advanced disease. In patients with metastatic cancer of the prostate, pain treatment often requires very large doses of either systemic or intraspinal opioids, often an insufficient pain treatment that produces undesirable side-effects (Cherny and Portenoy, Textbook of Pain, third edition, eds: P. D. Wall and R. Melzack, pages 787–823, 1994). Clearly, a better understanding of the mechanisms that mediate the sensation of pain associated with neuropathy and cancer pain will lead to new target identification and the development of more beneficial pain treatments.

SUMMARY OF THE INVENTION

The invention provides a method of determining whether a compound alleviates vasoconstriction-independent nerve pain mediated by endothelin-1 (ET-1). The method involves (i) determining whether the compound has the ability to inhibit a vasoconstriction-independent ET-1 action, and, if the compound has the inhibitory ability, then ii) determining whether the compound reduces vasoconstriction-independent nerve pain by testing the compound in human patients suffering from pain mediated by the vasoconstriction-independent ET-1 action.

The method of determining whether the compound has the ability to inhibit a vasoconstriction-independent ET-1 action can involve an in vitro assay composed of steps such as the following: (i) layering functional ET or $ET_A$ receptors, e.g. in samples of neuronal or vascular cells or neuronal or vascular cell membrane preparations, onto culture plates, e.g., scintillator-coated 96-well plates, in paired samples that contain or lack the compound; (ii) adding ET receptor ligand, e.g. [$^{25}$I]ET-1, measure specific binding, and assess ability of compound to inhibit ligand binding; if inhibitory compounds are identified, then (iii) further characterizing the agonist or antagonist effect of the compound on the activation of intracellular signaling, e.g. on G-protein coupled signaling, in cell-based assays; if ligands with antagonist or partial antagonist activity are identified, then (iv) screening compounds in an in vivo model, e.g., the direct sciatic nerve ET-1 application model, and assessing the effects on ET-1 induced pain behavior, e.g., hindpaw flinching.

Preferably, the compound inhibits the ET-1 action at a nerve ET receptor. Most preferably, the compound inhibits the ET-1 action at a nerve $ET_A$ receptor.

The invention also includes a method of treating a human patient to alleviate pain caused by vasoconstriction-independent ET-1 action. The method involves administering an effective amount of an ET inhibitor, e.g. an inhibitor from the group of sulfisoxazole, TBC-11251, BQ-123 (American Peptide Co., Sunnyvale, Calif.; Clinalfa AG, Switzerland), PD 156707 (Parke Davis, Morris Plains, N.J.), A-127722 (Abbott Laboratories, Abbott Park, Ill.), LU 135252 (Knoll Pharmaceutical Co., Mount Olive, N.J.), BQ-788 (American Peptides Co., Sunnyvale, Calif.), bosentan (Hoffman LaRoche, Nutley, N.J.), TAK-044 (Takeda Chemical Industries Ltd., Osaka, Japan), SB 209670 (Smith Klein Beecham Pharmaceuticals, Philadelphia, Pa.), and SB 217242 (Smith Klein Beecham Pharmaceuticals, Philadelphia, Pa.) as described in Ann. Reports in Medicinal Chemistry, Section II, Ch. 7, Endothelin Inhibitors, pages 61–70, 1997 (ed. A. M. Doherty, Academic Press, Inc.).

The structures of the aforementioned ET-1 antagonists are provided below.

3 sulfisoxazole

TBC-11251

LU 135252

PD 156707

BQ-788

4

-continued

A-127722

Bosentan

SB 209670

TAK-044

BQ-123

SB217242

Preferably, the ET inhibitor is an $ET_A$-selective inhibitor from the group of TBC-11251, BQ-123, PD156707, A-127722, and LU 135252, and the compound inhibis ET-1 action at a $ET_A$ receptor on the nerve.

The method of treatment of the invention can be used to alleviate pain in a patient with a condition associated with increased ET-1 levels and for the treatment of diseases such as metastatic prostate cancer, metastatic breast cancer, sickle cell anemia, and other painful vascular diseases, e.g., migraine headaches, Reynaud's disease, and peripheral vascular disease.

The invention also includes a method of determining whether a compound alleviates pain caused by nerve injury in human patients. The method involves (i) determining whether the compound has the ability to inhibit an inflammatory leukocyte response, and, if the compound has the inhibitory ability, then (ii) testing the compound in human patients suffering from pain caused by nerve injury to determine whether the compound alleviates the pain.

The method of determining whether the compound has the ability to inhibit an inflammatory leukocyte response can by carried out by conducting an in vitro assay, such as (i) harvesting leukocytes, e.g. rat leukocytes, and (ii) placing leukocytes in wells of a culture plate, e.g., a radially-distributed agarose culture plate, in paired samples which either contain or lack the compound, adjacent to wells containing minced nerve samples, e.g. minced rat sciatic nerve, (iii) incubating the plates for sufficient time, e.g. 8–12 hours, to allow leukocyte migration toward the nerve sample well, (iv) fixing and staining the leukocytes, and (v) quantifying the degree of leukocyte migration to assess the ability of the compound to inhibit leukocyte migration.

The invention also provides a method of treating a human patient to alleviate pain caused by nerve injury. The method involves administering an effective amount of a leukocyte migration inhibitor, e.g., itraconazole, mepaerine, ketoconazole, chloroquine, hydroxychloroquine, dipyridamole, or piroxicam (Feldene®, Pfizer, Inc., New York, N.Y.).

One advantage of the present invention is the identification of specific, novel targets to use for developing new pain treatments. Given these targets, candidate compounds never before considered as effective pain treatments can be analyzed. For example, using these new targets, screening assays can be performed to identify new candidate compounds previously missed in other anti-pain screens. In addition, compounds that have previously been identified as affecting the targets of the invention, i.e., compounds identified as ET inhibitors and leukocyte migration inhibitors, can be reanalyzed for their ability to alleviate pain.

Other features and advantages of the invention will be apparent from the following detailed description thereof, and from the claims.

BRIEF DESCRIPTION OF THE DRAWINGS

FIGS. 8A and 8B are graphs showing a comparison of mean latencies to hindpaw withdrawal from a thermal painful stimulus in CCI rats receiving saline (FIG. 8A), or 1.5 mg/kg/day dexamethasone (DEX) (ip) (FIG. 8B). In FIG. 8A, hindpaw withdrawal latencies ipsilateral to CCI are reduced from 3–10 days in saline-treated rats (p<0.005, Wilcoxon Signed Rank test). In FIG. 8B, hindpaw withdrawal latencies to CCI are unchanged from baseline and not different between hindpaws until 10 days after CCI in DEX-treated rats, when compared with saline-treated rats (p<0.05, ANOVA).

FIGS. 10A and 10B are graphs showing the effect of cyclophosphamide treatment (100 mg/kg., ip, on alternate days×3 days, prior to CCI) on mean latencies to hindpaw withdrawal from a thermal painful stimulus prior to and following sciatic nerve CCI. In FIG. 10A, hindpaw withdrawal latencies ipsilateral to CCI appear reduced from 3–10 days in saline-treated rats. In FIG. 10B, hindpaw withdrawal latencies to CCI are not different between hindpaws until 10 days after CCI in CYCLO-treated rats, when circulating leukocyte counts have recovered to near normal values.

DETAILED DESCRIPTION OF THE INVENTION

ET-1 Mediated Pain

We applied ET-1 and other drugs directly to the sciatic nerve in rats. Hindpaw flinching, a marker of pain behavior (Dubuisson and Dennis, Pain 4: 161–174, 1977), was used to quantify the pain response. The results of these experiments (described in detail below) led to the discovery that ET-1 acts directly at the nerve and elicits pain, at least in part, through a vasoconstriction-independent mechanism.

Methods

Surgical Procedures. Adult male Sprague Dawley rats (175–225 g) were anesthetized with an intermediate-onset, short-acting volatile anesthetic (Sevaflurane, Abbott Laboratories, North Chicago, Ill.). After shaving of the hair over the left or right flank and incision of the skin, blunt dissection was made through the biceps femoris, the sciatic nerve exposed by careful microdissection away from the surrounding connective tissue, and gently elevated by insertion of a small curved hemostat placed beneath it. Following drug administration, as described below, the biceps femoris was closed with a single silk suture, and the skin closed with surgical staples.

Drug administration. The following drugs were applied epineurially: 1) 40–800 μM endothelin-1 (ET-1) (synthetic, 98% pure peptide content, American Peptides Co., Sunnyvale, Calif.); 2) the selective endothelin-A receptor antagonist, BQ-123 (American Peptides Co.; Sunnyvale, Calif.) at 3 mM; 3) the selective endothelin-B receptor antagonist, BQ-788 (American Peptides Co.; Sunnyvale, Calif.) at 3 mM; and 400 μM epinephrine (American Regent Laboratories, Inc., Shirley, N.Y.).

All drugs were dissolved in phosphate buffered saline (PBS, pH=7.4), and applied in 40 μl volumes to the epineurial surface of the exposed sciatic nerve (n=10 rats/condition). The total time for each drug application was 3–4 min. BQ-123 and BQ-788 were applied in 3 stages: 20 min prior to, 10 min prior to and 30 sec before ET-1 application. PBS was administered to control animals. Excess drug or PBS solution was absorbed by cotton gauze placed at the edge of the exposed nerve.

Morphine was administered systemically immediately before anesthesia (10 mg/kg, ip). Naloxone was administered systemically 20 min after the completion of ET-1 application (2 mg/kg, ip).

In experiments involving repeated administration of ET-1, animals were re-anesthetized 75–80 min after surgery (time point after which no further hindpaw flinching was observed, as described below), and 400 μM ET-1 was applied in the same volume, as described above. Behavioral evaluation was performed, as described below, for an additional 60 min.

Behavioral evaluation. After 5 min, the rats demonstrated complete recovery from the effects of general anesthesia. Behavioral measurements were then performed with animals freely moving on a flat surface enclosed by an inverted large Plexiglas cage. The total number of ipsilateral and contralateral spontaneous hindpaw flinches (operationally defined as complete lifting of the hindpaw off the testing surface) were counted for consecutive 5 minute periods for a total 60 minute observation period. The total duration of hindpaw lifting and time spent exploring were also recorded.

Microfluorometry in E1A cells. E1A cells (retrovirally-transformed rat dorsal root ganglion cells) were grown as a monolayer on poly-L-lysine coated coverslips in Dulbecco's modified eagle media supplemented with 10% fetal bovine serum at 37° C. in a humified atmosphere (5% $CO_2$–95% air). Cells were used 48–72 hours after plating, at a confluence of 75 to 90%. The concentration of intracellular calcium was determined by dual excitation microfluorometry, using the calcium sensitive dye Fura-2 (Grynkiewicz, et.al., J. Biol. Chem. 260: 3440–3450, 1985). E1A cells were washed once with D-PBS (with $Ca^{++}$) and then incubated for 30 min at room temperature in D-PBS (with $Ca^{++}$) containing 7.5 μM Fura-2/AM and 0.00125% (wt/vol) pluronic-DMSO. The cells were then washed twice in D-PBS (with $Ca^{++}$) and incubated for an additional 30 minutes to allow cleavage of the Fura-2/AM to the active Fura-2.

Experiments were conducted with the coverslips in a perfusion chamber of 0.4 ml, with a constant flow rate of 4 ml/min. Each coverslip was equilibrated in D-PBS for 2 min prior to beginning an experiment. ET-1 was delivered into a catheter attached to the perfusion chamber such that the lag time from addition of ET-1 until it reached the perfusion chamber was about 30 sec. ET-1 was given as a pulse in a 400 μl volume.

Microfluorometry was performed with an inverted epifluoroscence microscope connected to a light source which provided two alternating wavelengths (Photon Technology International Deltascan). The excited wavelengths were 340 and 380 nm. Emitted light was passed through a 510 nm interference filter to a photomultiplier tube. Background fluorescence was subtracted from each trial.

Data Analysis. The peak frequency of hindpaw flinching, effects at 10 min post-drug administration, and area-under-the-curve (without approximation) from 0–60 min were all used to describe response-concentration functions.

Statistical analysis of differences between groups was performed by two-tailed Student's t-test, ANOVA, factorial ANOVA, and Fisher's Protected Least Significant Difference test (STAT View, SAS Statistical Institute, Cary, N.C.).

Results

Figure 1:
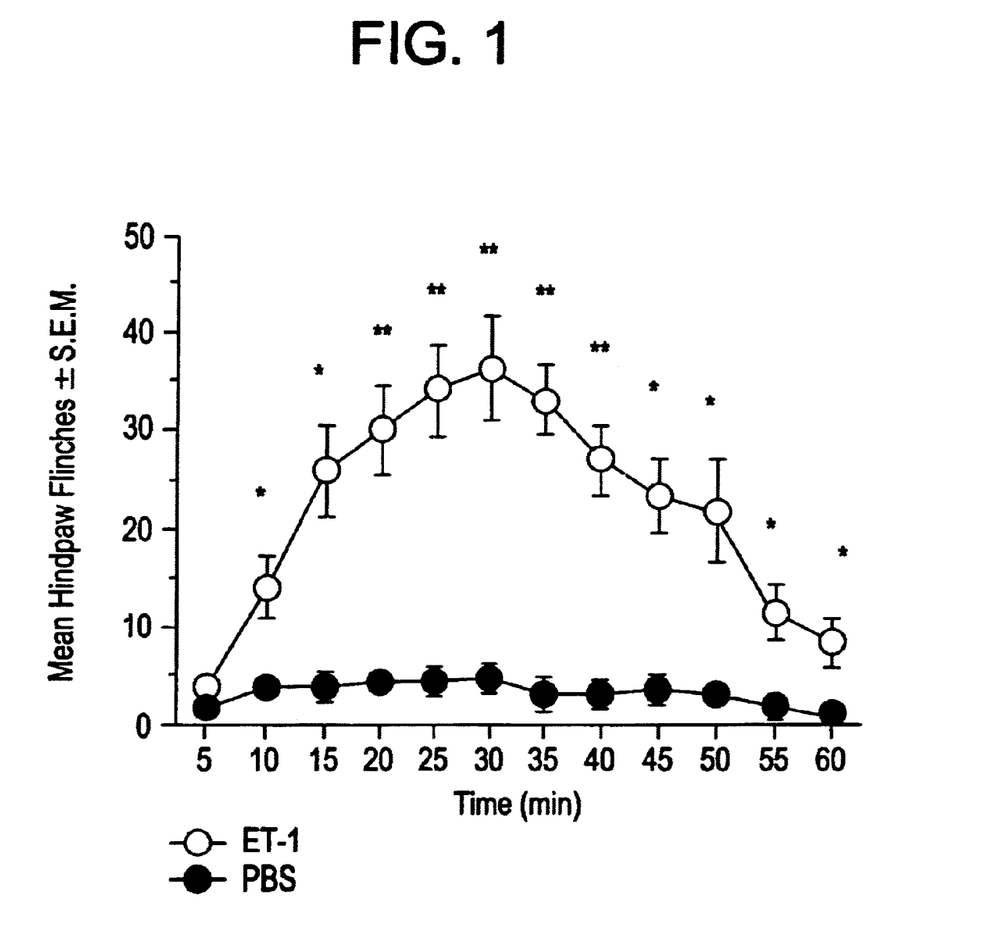
FIG. 1 is a graph showing the effect of 400 μM ET-1 applied at t=−5 min on the frequency of hindpaw flinching over a period of 60 min. Significant differences (*$p \leq 0.05$; **$p \leq 0.0001$) in the magnitude of hindpaw flinching were observed at nearly every time point when ET-1 (n=10) and PBS (n=10) treated animals were compared.

ET-1 effects. Repetitive, spontaneous hindpaw flinching was increased in ET-1-treated rats from 10–60 min post-administration (FIG. 1). ET-1 administration also caused postural changes, i.e., flexion of the plantar toes and mild eversion of the foot. These postural changes are evidence of a partial sciatic motor neuropathy. The increased flinching behavior and the postural changes demonstrated similar time courses, both peaked by 30 min and resolved to near baseline by 60 min. At times, flinching behavior was associated with sustained elevation of the hindpaw lasting up to 2 minutes.

The hindpaw flinching was associated with a partial and reversible sciatic motor neuropathy, suggesting a direct ET-1 action on the nerve. A direct ET-1 action is supported by evidence that administration of the same concentration of ET-1 onto or into the muscles surrounding, but not innervated by, the sciatic nerve caused neither increased hindpaw flinching nor postural changes. Thus, the observed behavioral effect was not due to muscle irritation and ensuing motor hyperreflexia. However, animals did show signs of generalized distress (chromodacryorrhea, or red tears) following ET-1 application to the muscle.

Figure 2:
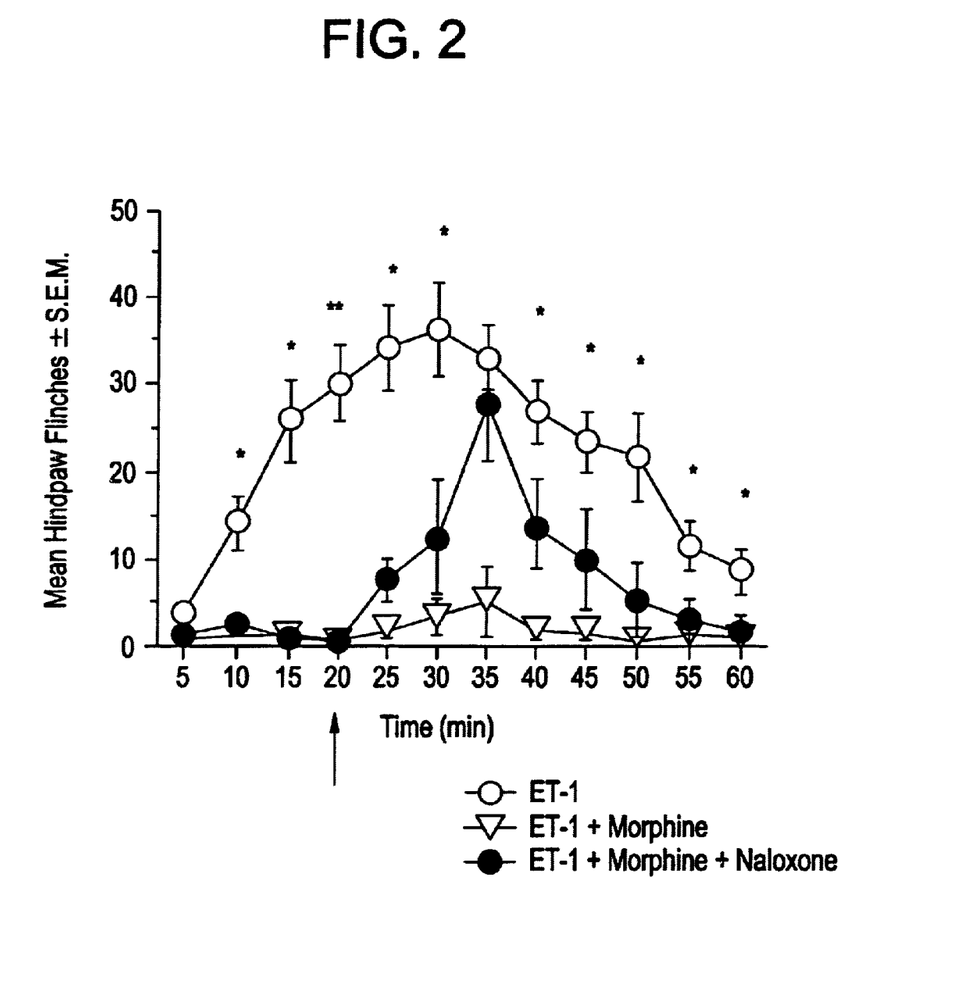
FIG. 2 is a graph showing the effect of systemic morphine (n=5) administered prior to ET-1 (n=10), and morphine+naloxone (n=5) on ET-1-induced hindpaw flinching. Differences between ET-1 and morphine-treated rats are present at all time points. Significant differences observed between ET-1 and morphine+naloxone-treated rats (*$p \leq 0.05$; **$p \leq 0.0001$). There is no difference between these groups 15 min after administration naloxone (arrow), consistent with a reversal of the effect of morphine at this time point. ET-1-treated animals are those described above in FIG. 1.

Effects of morphine and naloxone on ET-1 induced hindpaw flinching. Morphine (10 mg/kg, ip) was administered immediately before anesthesia and the frequency of hindpaw flinches counted. At this dose, morphine completely blocked flinching induced by ET-1 (FIG. 2). Naloxone (2 mg/kg, ip), administered 20 min after ET-1, rapidly reversed the effect of morphine for approximately 10 min (FIG. 2), consistent with naloxone's known short duration of action. Given the effects of morphine and naloxone, the following mechanisms are clear: 1) ET-1 induces pain behavior that is blocked by opioids, and 2) morphine blockade is mediated through an opioid receptor-dependent mechanism. Therefore, the pain behavior elicited by ET-1 was consistent with the pain associated with metastatic prostate cancer, which is also blocked by opioids. Animals in these experiments showed minimal signs of sedation, but only at the beginning of testing, as determined by their level of alertness and time spent in exploratory behavior.

Effects of epinephrine on hindpaw flinching. We applied epinephrine (400 $\mu$M) to sciatic nerve. This dose produces a maximal vasocontriction effect, yet no evidence of hindpaw flinching was observed thoughout the 60 min observation period. Therefore, the ET-1 induced increase in hindpaw flinching occurs independent of ET-1's vasoconstriction effect. Alternative sites of ET-1 action besides the microvessels include Schwann cells or sensory afferent neurons themselves.

Figure 3:
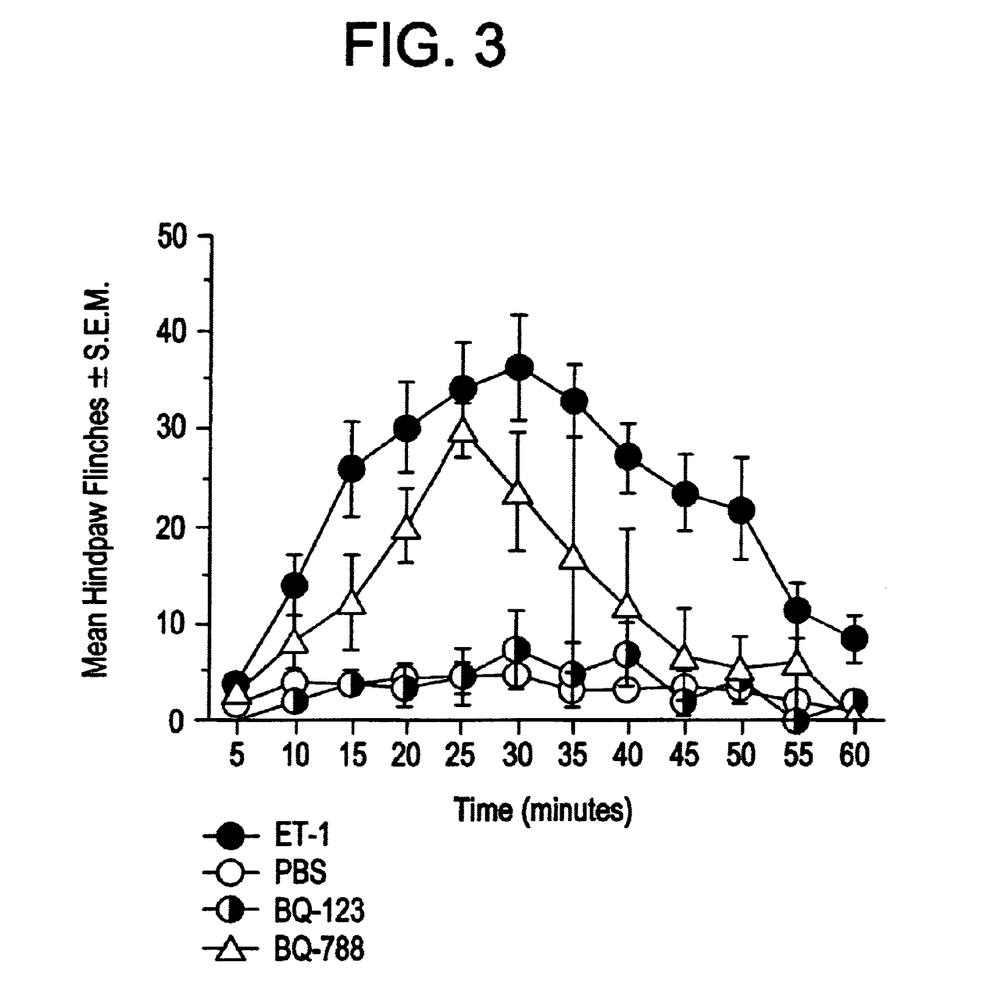
FIG. 3 is a graph showing the effect of BQ-123 (n=10) (3 mM) an d BQ-788 (n=4) (3 mM) administered 20, 10, and 0 min prior to ET-1 (400 μM) on ET-1-induced hindpaw flinching. Differences between BQ-123 and ET-1 are significant at every time point after 5 min. Differences between BQ-788 and ET-1-treated animals are significant at 45 and 50 min. Animals treated with ET-1 alone are those described above in FIG. 1.

ET-1 effects are $ET_A$ receptor-dependent. ET receptor subtypes, $ET_A$ and $ET_B$ are selectively antagonized by BQ-123 and BQ-788, respectively. BQ-123 completely blocked the ET-1 induced hindpaw flinching from 10–60 min post-ET-1 administration, whereas BQ-788 reduced hindpaw flinching significantly only at the 40 and 45 min timepoints (FIG. 3). The concentrations chosen for these antagonists (3 mM) were well in excess of their KI's in other tissues (Marsault et al., Am. J. Physiol. 264 (Cell Physiol. 33): C687–C693, 1993; Ishikawa et al., J. Med. Chem. 35(11): 2139–2142, 1992). These results indicate that the $ET_A$ subtype of receptor on neurons mediates the ET-1 induced pain behavior.

Figure 4A:
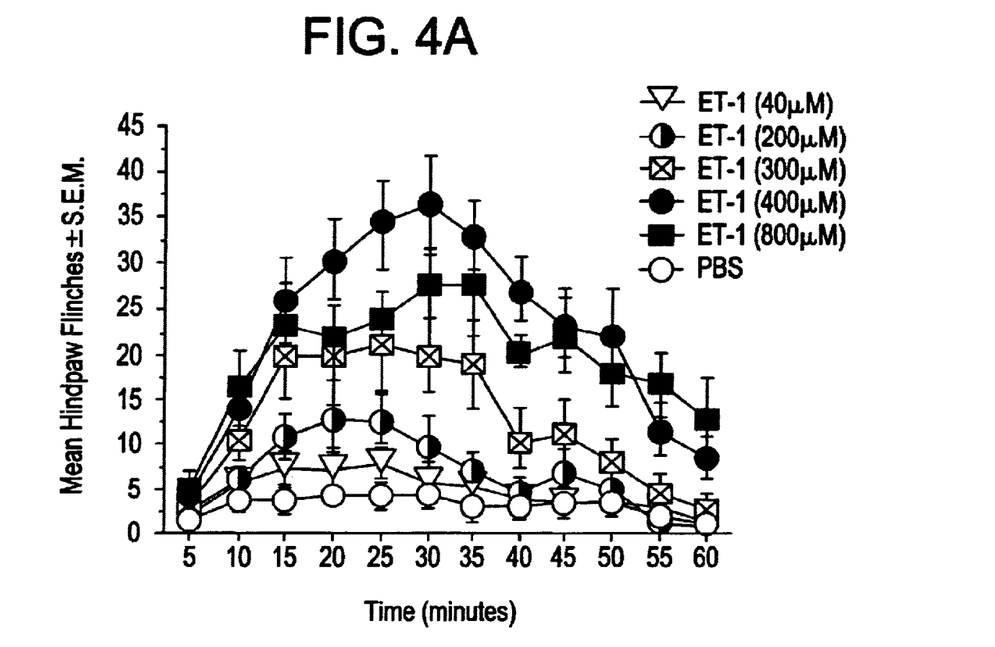
FIG. 4A is a graph showing the effect of applying 1.6, 8, 12, 16, and 32 nanomoles of ET-1 (equivalent to 40, 200, 300, 400, and 800 μM, respectively) onto rat sciatic nerve. The group treated with 16 nanomoles are those described above in FIG. 1.
Figure 4B:
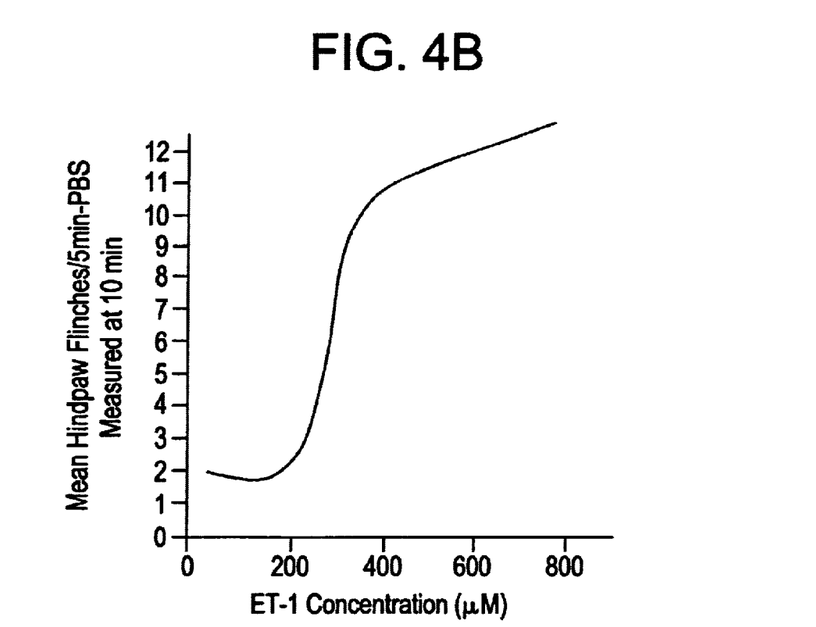
FIG. 4B shows the ET-1 dose response of hindpaw flinching at 10 minutes post ET-1 administration. The half-maximal effect is estimated to occur at a concentration of 300 μM.

Dose-dependent effects of ET-1. ET-1 was administered to sciatic nerve as previously described in concentrations ranging from 40–800 $\mu$M. The frequency of hindpaw flinching increased in a monotonic (at early time points), dose-dependent, non-linear fashion. The maximum frequency was achieved with 400 $\mu$M ET-1 (FIGS. 4A and B). The initial rate-of-rise in hindpaw flinching correlated with increasing ET-1 concentration. However, the time elapsed for peak response after ET-1 administration was longer for the higher concentrations (FIG. 4A).

Figure 5:
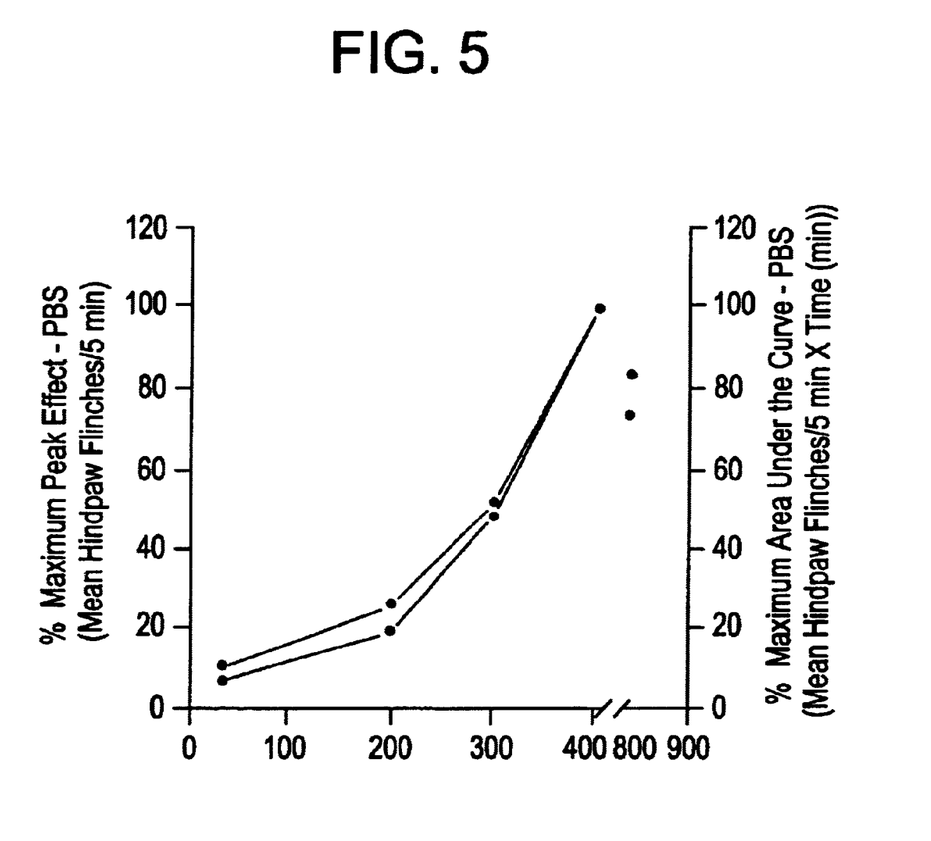
FIG. 5 is a graph showing the comparison of peak frequency of hindpaw flinching and the area-under-the-curve analysis for each concentration of ET-1.

Similar ET-1 behaviors were observed whether peak frequency effects or the area under the curve (AUC) were analyzed (FIG. 5). There was no evidence of receptor-limited effects (i.e. saturation), and overall determinations of concentrations producing a half-maximal effect were limited by the apparent inhibitory effect observed at high concentration (800 $\mu$M).

Figure 6:
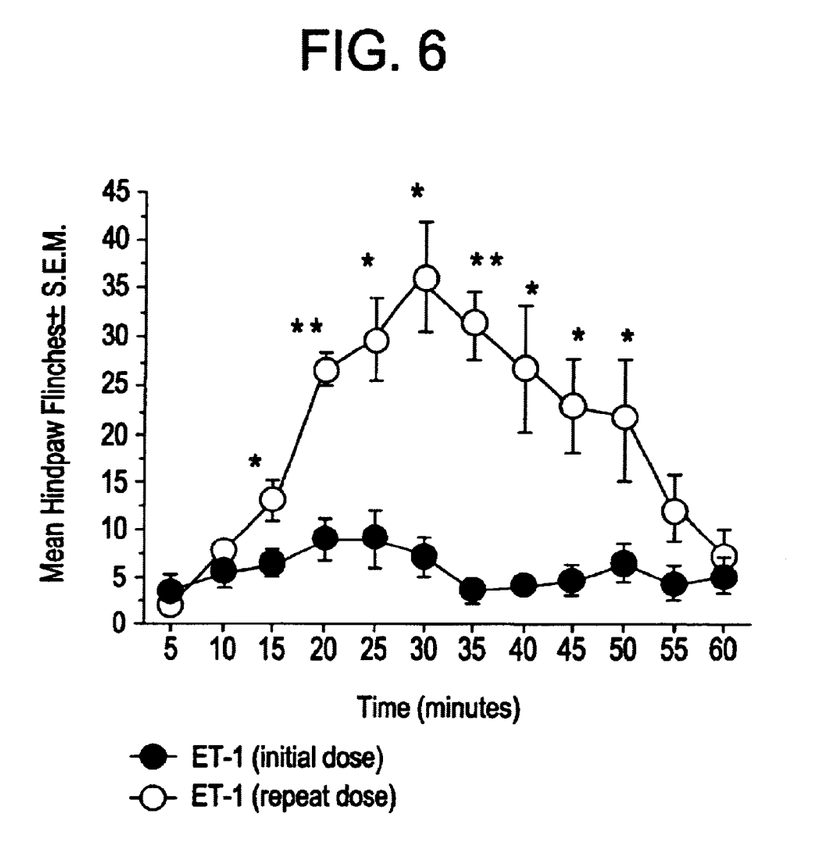
FIG. 6 is a graph showing the effect of repeat administration of 400 μM ET-1 on hindpaw flinching. Significant differences (*$p \leq 0.05$; **$p \leq 0.0001$) in the frequency of hindpaw flinching were observed at most time points when the initial and repeat dose groups were compared.

Effects of repeated administration. Following administration of ET-1 (400 $\mu$M) and a 60 min testing period, a second treatment of 400 $\mu$M ET-1 was administered 15–20 min after completion of the first testing period. The second ET-1 treatment did not produce hindpaw flinching that was significantly different from controls (as shown in FIG. 1) over the second, post-administration 60 min observation period (FIG. 6).

Figure 7:
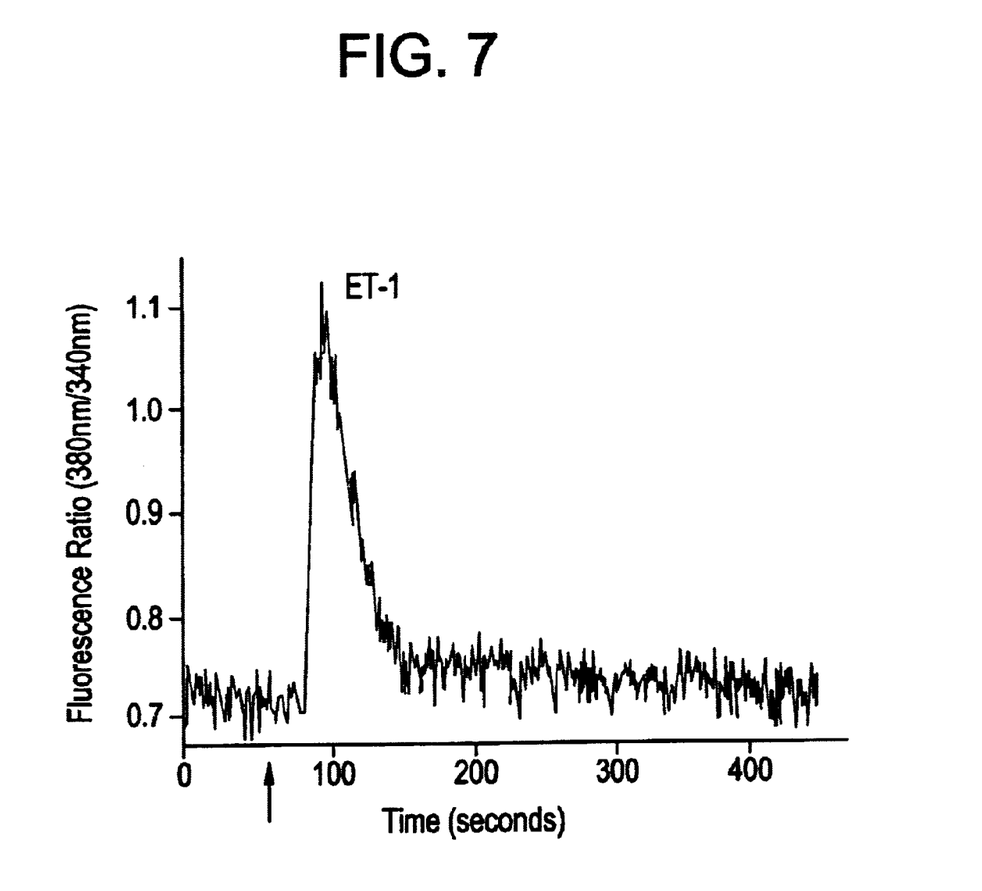
FIG. 7 is a graph showing the response of fura-2-loaded embryonic sensory neurons to the superfusion of 400 μl of 13.5 μM ET-1 in PBS (pH=7.4) into an 0.5 ml perfusion chamber. The arrow points to the time of application of ET-1.

ET-1 has a direct effect on neuron-derived cells in culture. Microfluorometry analysis in E1A cells during ET-1 administration revealed a large, rapid, and transient increase in Fura-2 fluorescence (FIG. 7). This increase demonstrates that ET-1 induced a rise in intracellular $Ca^{++}$ in the E1A cells from the normal resting level (50–100 nM) to near 500 nM. This change is as large as that produced by KCl (30 mM)-induced depolarization. These effects are further evidence that ET-1 produces a direct effect on neural tissue. Following ET-1, a slowly decaying plateau phase was present over the subsequent 5 min. This plateau is likely related to the diffusion of ET-1 across the perineurium.

Summary and Conclusions

The studies described above provide several important observations: 1) ET-1 applied to rat sciatic nerve in vivo induces ipsilateral hindpaw flinching behavior, a behavioral pain response; 2) systemic treatment with morphine prior to ET-1 administration blocks this flinching behavior, a blockade which is reversed by systemic naloxone, 3) concentrations of epinephrine known to induce the same degree of vasoconstriction in sciatic nerve as does ET-1 do not produce increased hindpaw flinching behavior that is different from vehicle, 4) the effects of ET-1 on hindpaw flinching are non-monotonically dose-dependent, and 5) ET-1 has a direct effect on neurons, increasing intracellular $Ca^{++}$ in cultured embryonic sensory neurons.

Given these results, we conclude that ET-1 applied to rat sciatic nerve 1) produces a direct effect on sensory neurons, and 2) induces pain behavior via a mechanism independent of vasoconstriction of sciatic nerve microvessels. Therefore, the inhibition of ET-1's vasoconstriction-independent mechanism of causing pain is an effective pain treatment, especially under conditions where ET-1 levels are elevated in a patient, such as metastatic prostate cancer. Furthermore, given that ET-1 acts directly on the sensory neuron $ET_A$ receptor, the $ET_A$ receptor is an important therapeutic target.

Leukocyte Infiltration-mediated Pain

We studied the role of leukocyte migration in eliciting nerve pain. Nerve injury was induced using the chronic constrictive injury procedure (CCI) on rat sciatic nerve. The results of these studies (described in detail below) led to the discovery that the pain response induced by nerve injury is correlated with leukocyte migration to the injury site. Furthermore, the pain response can be inhibited if leukocyte migration to the injury site is reduced.

Methods

CCI surgery. The sciatic nerve of a rat was exposed after blunt dissection of the biceps femoris. Four chromic gut ligatures (4-0) were placed around a 7 min section of sciatic nerve in the mid-thigh region. The ligatures were applied so that they constricted the diameter of the nerve just enough to impede circulation through the superficial vasculature (as visualized under an operating microscope at 40×). Sham-operated rats received an identical exposure of the left sciatic nerve without CCI. A coding system blinded the investigators to the nature of the surgery performed on individual rats.

Histology. To compare the extent and type of cellular inflammation around the peripheral nerve due to CCI between DEX- and saline-treated rats, the ligated sciatic nerve was processed for histological analysis. At 3, 5, 7, and 10 days post-CCI, animals were euthanized with 100 mg/kg intraperitoneal sodium pentobarbital, and then transcardially perfused first with 50 ml of cold 0.9% NaCl, 1 ml/g body weight of 4% paraformaldehyde in 0.01 M phosphate buffered saline, pH 7.4 (PBS). A 2–3 cm section of sciatic nerve, or a 1 cm section of L5 and L6 spinal nerves, which included material at the ligation site, as well as that just proximal and distal to ligation, was placed in 0.01 M PBS, 4% paraformaldehyde to post-fix for 2 hours. Tissue was then embedded in paraffin, cut in 10–30 $\mu$m sections on a vibratome, and placed on glass slides. Slides were deparaffinized and then hydrated in distilled water prior to staining in freshly filtered Harris' hematoxylin for 6–15 min. After washing in running tap water for 2–5 min, sections were differentiated in 1% acid alcohol, washed briefly in tap water, and then placed in weak ammonia water until sections are bright blue. The sections were then washed thoroughly in running tap water, transferred to 80% ethanol, and then counterstained in eosin-phloxine solution prior to dehydration and mounting with Permount.

Quantitation of leukocytes in nerve sections. To detect leukocytes in injured peripheral nerve, both cellular and nuclear stains (H and E, respectively) were used. To be included in the leukocyte cell count, leukocytes had to 1) have a nucleus which was clearly visible and characteristic of an infiltrating macrophage (bean-shaped nucleus), neutrophil (polymorphic nucleus) or lymphocyte (dense nucleus that fills the cytoplasm); 2) have a "foamy" macrophage appearance typical of a myelin-ingesting phagocytes; and 3) be present within the endoneurial space. Cells present within vascular spaces or containing nuclei that could not be clearly differentiated from activated Schwann cells, fibroblasts or endothelial cells were not counted.

Blood cell counts and replacement. To obtain syngeneic leukocytes for replacement in animals depleted of leukocytes as a result of CYCLO treatment, we centrifuged whole blood from normal rats (1500 rpm, 10 min, in a clinical centrifuge). The buffy coat (which contains primarily leukocytes) was removed under sterile conditions and injected into experimental animals.

Leukocyte counts were made at subsequent time points to determine the need for additional leukocyte supplementation. For CYCLO-treated animals, all the leukocytes in the buffy coat from one normal animal are needed to fully replenish those lost because of treatment. For CSF-treated animals, smaller numbers of leukocytes (a portion of buffy coat volume to be determined) are likely to be needed to augment the effect of CCI.

Complete blood counts were serially determined on all animals receiving treatments. Total white blood cell counts in normal rats are approximately $9 \times 10^3$ $\mu$l in normal animals, increase slightly in CCI rats, and are markedly reduced to $<1 \times 10^3/\mu$l in CYCLO-treated CCI rats.

Statistical analyses. Differences within groups were analyzed using the Wilcoxon signed rank test. Differences between groups were analyzed by two-way ANOVA and Fisher's protected least significant difference test for post-hoc comparisons.

Results

Figure 8A:
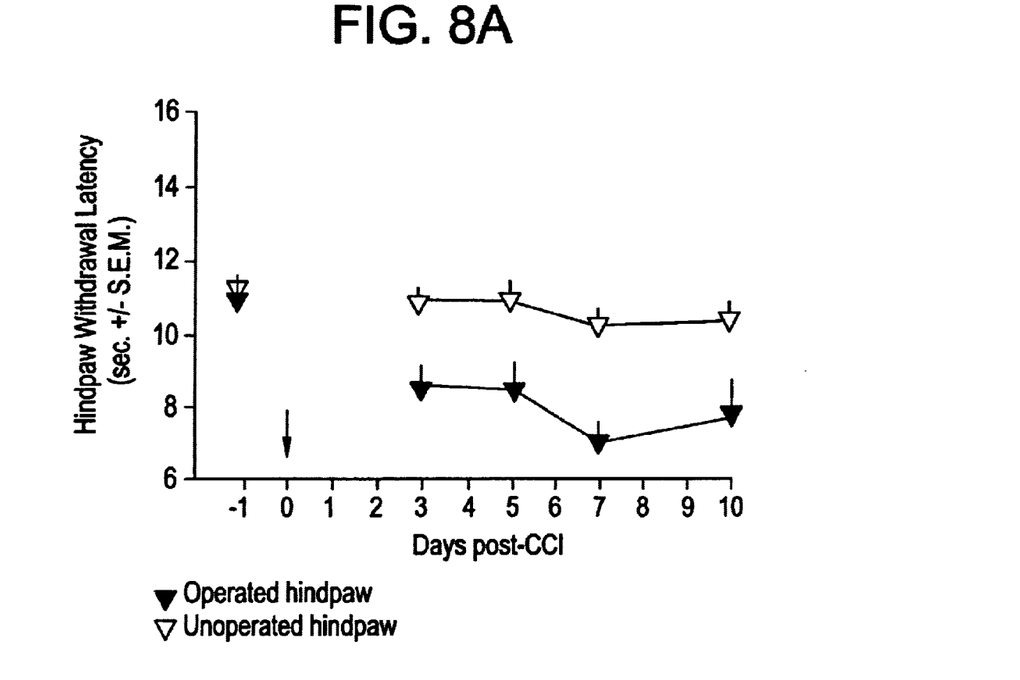
Figure 8B:
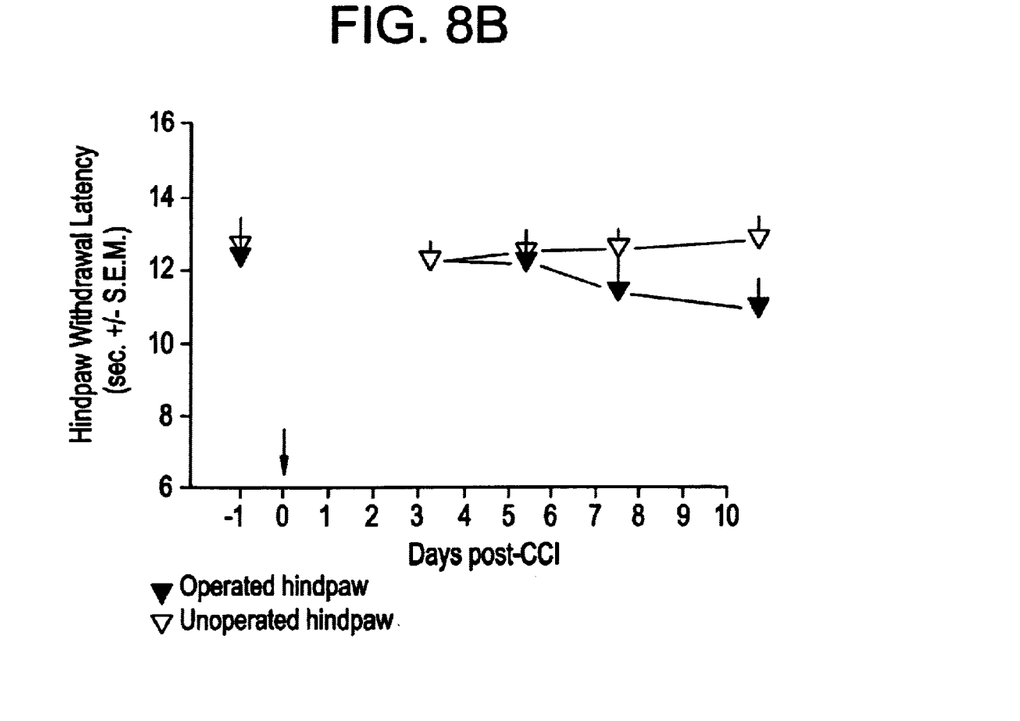

Dexamethasone inhibits CCI-induced pain sensitivity. Following a chronic constrictive injury (CCI) procedure on rat sciatic nerves, the rats demonstrated increased pain sensitivity (thermal hyperalgesia) in the ipsilateral hindpaw when compared to both baseline values and the contralateral hindpaw values (FIG. 8A). Thermal hyperalgesia was defined as a reduction in the latency to hindpaw withdrawal during a thermal stimulus applied to the plantar surface. Dexamethasone (DEX) (1.5 mg/kg, i.p.), administered to rats 24 hr prior to, and daily for 10 days after CCI, delayed the onset of thermal hyperalgesia when compared to CCI treatment alone (FIG. 8B), eliminating differences from both baseline values and contralateral hindpaw values for a duration of 3–7 days post-CCI. Presumably, chemotactic signals overwhelmed the effects of DEX by 10 days to account for differences from baseline and between hindpaws at this timepoint (FIG. 8B).

Figure 9:
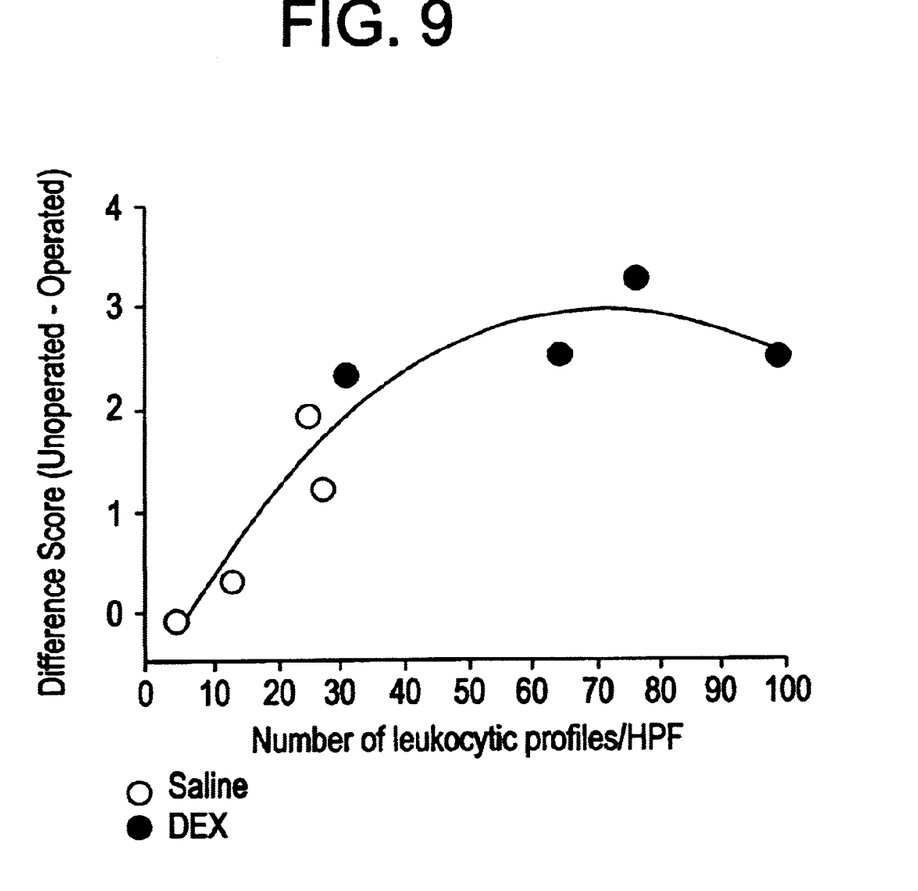
FIG. 9 is a graph showing a comparison of the mean number of leukocytic profiles per high power field (HPF) in representative 5 μm sections of sciatic nerve from saline- and DEX-treated CCI rats, and the mean difference (unoperated-operated) in hindpaw withdrawal latencies from 3–10 days. Small increases in leukocyte number above baseline are associated with minimal differences in hindpaw withdrawal latency. As numbers increase, the difference scores increase quickly and reach a plateau beyond which further increases in leukocyte number do not affect withdrawal latency.

Dexamethasone inhibits CCI-induced leukocyte migration. Most significantly, DEX also delayed the onset of the leukocytic inflammatory response to CCI (Table I). Comparison of leukocyte infiltration and hindpaw withdrawal latencies (FIG. 9) revealed that hyperalgesia (seen at 3 days in saline-treated CCI rats and at 7 days in DEX-treated rats) emerged when about 25–30 leukocytes/40× high power field (HPF) (or approximately $10^5$ cells/7 mm segment of intact nerve) were present in the region of the nerve injury. Given that there was no hyperalgesia in DEX-treated animals when there were <13 leukocytes/40× HPF (approximately $5 \times 10^4$/7 mm segment of intact nerve), it is likely that a threshold number of leukocytes is required for the development or maintenance of sustained hyperalgesia.

Figure 10A:
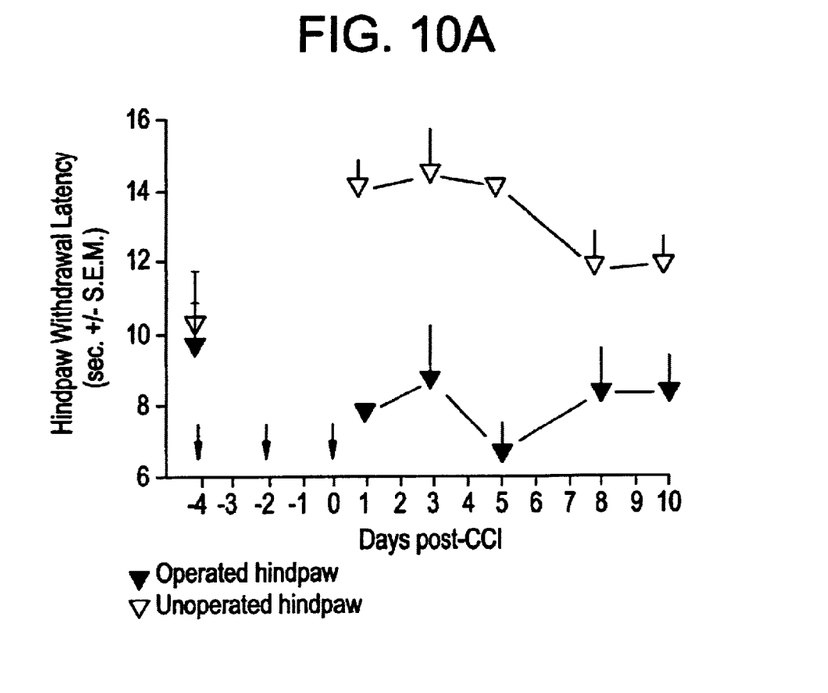
Figure 10B:
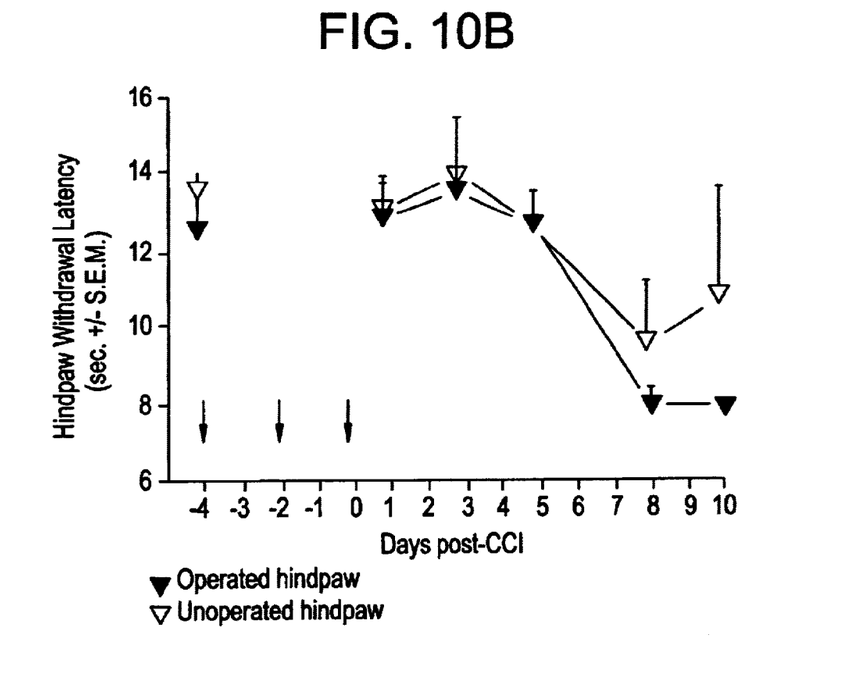

Cyclophosphamide treatment inhibits CCI-induced leukocyte infiltration and hyperalgesia. As another means of reducing the leukocyte inflammation response, the alkylating agent cyclophosphamide (CYCLO) (Sigma, St. Louis, Mo.) was pre-operatively administered (100 mg/kg on alternate days×3 days), and markedly reduced circulating leukocyte numbers. In CCI-treated rats, CYCLO also blocked the hyperalgesia response, until leukocyte counts returned toward normal 10 days post-surgery (FIGS. 10A, 10B, and Table II).

TABLE I

Number of leukocytic profiles over time in sciatic nerve in rats with a chronic constriction injury*

| | Time post-CCI | | | |
|---|---|---|---|---|
| Treatment | 3 days | 5 days | 7 days | 10 days |
| Saline | 31.5 ± 9.5 | 99.9 ± 30.5 | 77.3 ± 16.9 | 65.0 ± 10.3 |
| DEX** | 4.2 ± 0.92 | 12.8 | 23.3 ± 26.9 | 25.7 ± .9*** |

*The number of leukocytic profiles within six high-power fields (0.238 mm$^2$) was determined in regions proximal, within and distal to nerve ligation. Rats were treated with either saline or dexamethasone (DEX). Nerves from 2 rats at each time point were examined (n = 1 for DEX at 5 days post-CCI). Data are expressed as mean ± S.D.
**Overall the difference between groups (data from 5 day time point excluded) approaches statistical significance (ANOVA, p = .0504).
***There is a significant difference between saline and DEX-treated CCI rats at 10 days (p < .05, Wilcoxon Signed Rank Test).

TABLE II

Mean number of leukocytes ($10^3$/ml) following cyclophosphamide (100 mg/kg) treatment

|  | Baseline | 1 day | 3 days | 5 days | 8 days | 10 days |
|---|---|---|---|---|---|---|
| Saline | 9.2 ± 0.7 | 12.3 ± 1.1 | 12.7 ± 1.0 | 13.5 ± 1.8 | 13.6 ± 1.5 | 11.1 ± 0.6 |
| Cyclophosphamide | 9.2 ± 0.7 | 0.4 ± 0.1 | 1.0 ± 0.3 | 0.5 ± 0.4 | 4.6 ± .6 | 7.3 ± 1.8 |

Figure 11A:
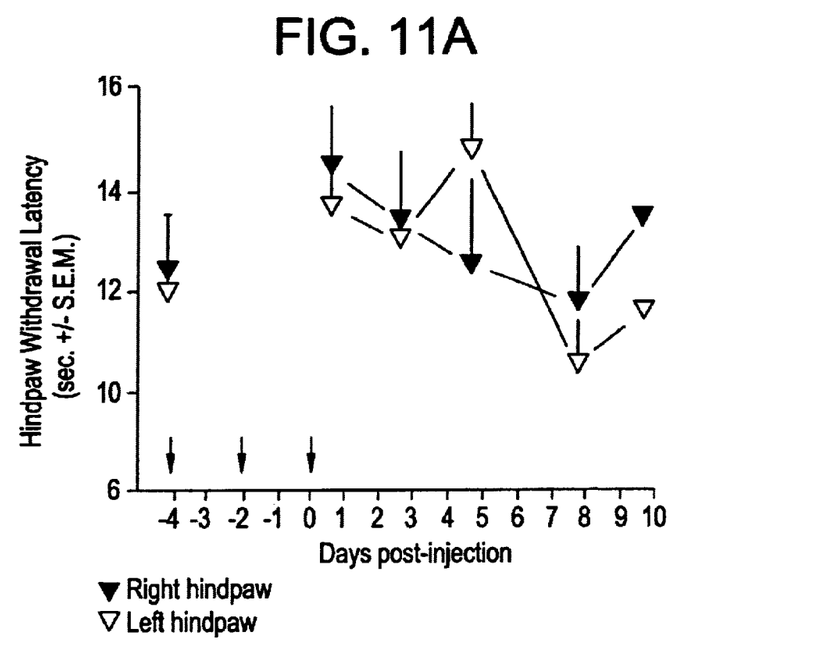
FIGS. 11A and 11B are graphs showing the comparable effects of saline (FIG. 11A) and cyclophosphamide (FIG. 11B) treatment on hindpaw withdrawal latencies to thermal stimulation in normal rats. Although no apparent differences between hindpaws were observed in either treatment group, a trend toward bilateral hyperresponsiveness was seen in both groups and was likely due to handling (multiple injections). For these experiments only, different groups of treated animals were tested (alternating fashion) on each test day to limit the amount of blood drawn.
Figure 11B:
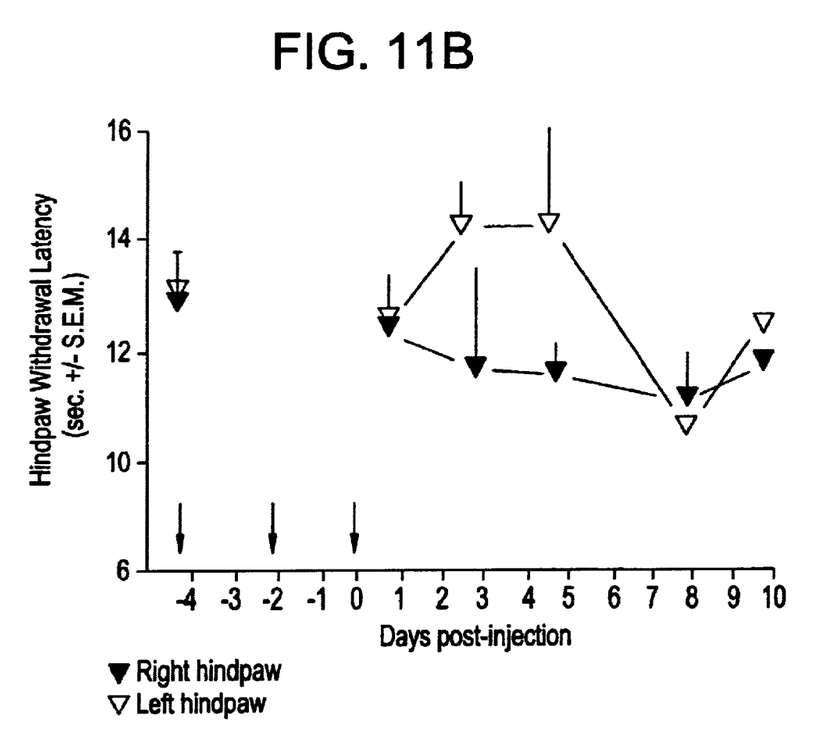

This effect was not caused by CYCLO-associated toxicity, because CYCLO had no analgesic effects with respect to thermal pain stimulation in normal animals (FIGS. 11A and B).

Anti-CD18 antibody treatment inhibits CCI-induced hyperalgesia. Systemic administration of an anti-CD18 antibody (WT.3) 1 day pre-CCI to 6 days post-CCI completely blocked pain behavior in the rats for this period of time.

Summary and Conclusions

As the following results demonstrate, the leukocytic inflammatory response plays a significant role in mediating the pain behavior that follows CCI in the rat. This conclusion results from the following experimental results: 1) suppression of leukocyte chemotaxis and activity, via dexamethasone treatment, blocks hindpaw thermal hyperalgesia in CCI rats until intraneural leukocytes reach a 'threshold' value; and 2) depletion of leukocytes in CCI rats with cyclophosphamide or anti-CD18 antibody also block hyperalgesia in CCI rats until circulating leukocyte counts recover.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method of determining whether a compound alleviates vasoconstriction-independent nerve pain mediated by endothelin-1 (ET-1) in a human patient in need thereof, said method comprising the steps of:
    a) determining whether said compound has endothelin-1 antagonist or partial antagonist activity, and then, if said compound has said activity,
    b) testing said compound in human patients suffering from pain mediated by vasoconstriction-independent ET-1 action to determine whether the compound alleviates said pain.

2. The method of claim 1, wherein step (a) comprises conducting an in vitro assay.

3. The method of claim 1, wherein the site of said vasoconstriction-independent ET-1 action is at a nerve ET receptor.

4. The method of claim 3, wherein said nerve ET receptor is an $ET_A$ receptor.

* * * * *